United States Patent

Daugherty et al.

[11] Patent Number: 5,427,952
[45] Date of Patent: Jun. 27, 1995

[54] ANALYTICAL METHOD FOR NONMETALLIC CONTAMINATES IN SILICON

[75] Inventors: Richard D. Daugherty, Hanover; Roland L. Halm, Madison, both of Ind.; Charles S. Kuivila, Crestwood, Ky.

[73] Assignee: Dow Corning Corporation, Midland, Mich.

[21] Appl. No.: 165,567

[22] Filed: Dec. 13, 1993

Related U.S. Application Data

[63] Continuation of Ser. No. 3,041, Jan. 11, 1993, abandoned.

[51] Int. Cl.⁶ .......................................... C01B 33/037
[52] U.S. Cl. ........................................ 436/72; 436/75; 436/79; 436/80; 420/578; 423/348
[58] Field of Search ............... 423/348; 436/72, 75, 436/79, 80; 420/578

[56] References Cited

U.S. PATENT DOCUMENTS

| | | | |
|---|---|---|---|
| 2,380,995 | 8/1945 | Rochow | 556/472 |
| 2,380,996 | 8/1945 | Rochow | 556/472 |
| 3,372,993 | 3/1968 | Brown | 436/78 X |
| 4,151,264 | 4/1979 | Mori et al. | 423/348 |
| 4,246,249 | 1/1989 | Dawless | 423/348 |
| 4,256,717 | 3/1981 | Dawless | 423/348 |
| 4,298,423 | 11/1981 | Lindmayer | 423/348 X |
| 4,312,846 | 1/1982 | Dawless | 423/348 |
| 4,388,286 | 1/1983 | Kapur et al. | 423/348 |
| 4,752,327 | 6/1988 | Lee et al. | 75/624 X |
| 4,822,585 | 4/1989 | Dawless | 423/348 |

OTHER PUBLICATIONS

Clark, J., Organometallic Chemistry, 376:165–222 (1989).

Primary Examiner—Donald E. Czaja
Assistant Examiner—Milton I. Cano
Attorney, Agent, or Firm—William F. Boley

[57] ABSTRACT

The present invention is a method for analyzing silicon for nonmetallic contaminants. The method comprises: (A) forming an alloy comprising silicon and a metal which promotes separation of nonmetallic contaminants present in the alloy, (B) separating the nonmetallic contaminants from the alloy, and (C) analyzing the separated nonmetallic contaminants for chemical content. The present invention is particularly useful for analyzing metallurgical grade silicon intended for use in the direct process for the production of organohalosilanes for the presence of oxides and carbides of calcium, aluminum, and silicon.

25 Claims, No Drawings

ANALYTICAL METHOD FOR NONMETALLIC CONTAMINATES IN SILICON

This is a continuation of application Ser. No. 08/003,041 filed on Jan. 11, 1993 now abandoned.

BACKGROUND OF INVENTION

The present invention is a method for analyzing silicon for nonmetallic contaminants. The method consisting essentially of:

(A) forming an alloy comprising silicon and a metal which promotes separation of nonmetallic contaminants present in the alloy, (B) separating the nonmetallic contaminants from the alloy, and (C) analyzing the separated nonmetallic contaminates for chemical content.

The present invention is especially useful for analyzing metallurgical grade silicon intended for use in the direct process for the production of organohalosilanes for the presence of oxides and carbides of calcium, aluminum, and silicon.

Organohalosilanes, particularly dimethyldichlorosilane, are important intermediates in the silicone industry. The organohalosilanes are typically hydrolyzed and condensed to form polyorganosiloxanes which can then be processed to form, for example, silicone fluids, elastomers, and resins. The predominant commercial process for preparing these organohalosilane intermediates is one commonly referred to as the "direct process," as originally described by Rochow, U.S. Pat. No. 2,380,995 issued Aug. 7, 1945, and Rochow et al., U.S. Pat. No. 2,380,995, issued Aug. 7, 1945.

Because of the high volume of organohalosilanes used in the silicone industry, considerable effort has been devoted to optimizing the conversion of the silicon to the organohalosilanes, particularly diorganodihalosilanes. It is known in the silicone industry that different lots of metallurgical grade silicon react differently in the direct process.

To attempt to control the lot-to-lot variability of the reactivity of metallurgical grade silicon in the direct process, manufacturers of organohalosilanes have set strict controls on the acceptable types and levels of contaminants present in the silicon. Clarke, J., Organometallic Chemistry, 376:165-222 (1989), provides a comprehensive review of the direct process for synthesis of methylchlorosilanes and the effects of contaminants on the process.

The present inventors believe that a significant cause of the lot-to-lot variability in the reactivity of metallurgical grade silicon in the direct process is the presence of nonmetallic contaminants in the silicon, such as oxides and carbides of calcium, aluminum, and silicon. While these oxides and carbides are believed detrimental to the direct process, low levels of certain metallic species containing these metals are considered to be beneficial to the direct process.

Standard methods for analyzing metallurgical grade silicon for contaminants involves an elemental analysis of the bulk of the silicon for elements such as calcium and aluminum. Therefore, these methods of analysis do not distinguish between, for example, calcium and aluminum which may be present in the metallurgical grade silicon as metallic species and calcium and aluminum which may be present in the silicon in a detrimental nonmetallic form.

An objective of the present invention is to provide a method where nonmetallic forms of elements, such as calcium, aluminum, and silicon can be distinguished from the other forms in silicon. The inventors have found that alloying the silicon with a metal which promotes separation of nonmetallic contaminants present in the alloy provides a method where the nonmetallic contaminants can be separated from the alloy and analyzed by standard methods for their elemental contents.

SUMMARY OF INVENTION

The present invention is a method for analyzing silicon for nonmetallic contaminants. The method consisting essentially of:

(A) forming an alloy comprising silicon and a metal which promotes separation of nonmetallic contaminants present in the alloy, (B) separating the nonmetallic contaminants from the alloy, and (C) analyzing the separated nonmetallic contaminants for chemical content.

The present invention is particularly useful for analyzing metallurgical grade silicon intended for use in the direct process for the production of organohalosilanes for the presence of oxides and carbides of calcium, aluminum, and silicon.

DESCRIPTION OF INVENTION

The present invention is a method for analyzing silicon for nonmetallic contaminants. The method consisting essentially of:

(A) forming an alloy comprising silicon and a metal which promotes separation of nonmetallic contaminants present in the alloy, (B) separating the nonmetallic contaminants from the alloy, and (C) analyzing the separated nonmetallic contaminants for chemical content.

In the present method nonmetallic contaminants are separated from silicon. A preferred silicon for use in the method is metallurgical grade silicon. By "metallurgical grade" silicon, it is meant a silicon comprising from 98 weight percent or greater silicon to less than 100 weight percent silicon. Preferred is refined metallurgical grade silicon. Even more preferred is when the metallurgical grade silicon has been refined by an oxidative process. For example, the molten silicon can be refined by contacting with oxygen, air, or an oxidative compound such as silicon dioxide. In a preferred refining process, the molten silicon is contacted with oxygen or air in the presence of one or more slag components.

The silicon is alloyed with a metal which promotes separation of nonmetallic contaminants present in the alloy. The alloying can be accomplished by standard methods for alloying metals. For example, a mixture of silicon and the alloying metal can be formed and the mixture heated in an induction furnace to a temperature sufficient to form a melt of the silicon and the alloying metal. When copper is the alloying metal a preferred temperature for alloying is within a range of about 1100° C. to 1500° C. When copper is the alloying metal an even more preferred temperature for alloying is within a range of about 1300° C. to 1450° C.

It is preferred that the alloying be accomplished in an inert atmosphere, for example, under an argon blanket. This reduces the potential for the formation of nonmetallic compounds during the alloying process and allows a more accurate determination of nonmetallic contaminants present in the bulk silicon from which the alloying sample was taken. The metal which promotes separation of nonmetallic contaminants present in the alloy, hereafter referred to as the alloying metal, can be any metal having the following general characteristics: low-temperature melting point, miscibility in the molten state with silicon, low vapor pressure at molten alloy temperature, makes specific gravity of molten alloy different from nonmetallic contaminants in the alloy, and creates a low-temperature melting point alloy. Generally, the term "low-temperature" refers to those alloying metals and alloys having a melting point less than that of silicon. The alloying metal can be, for example, selected from a group consisting of aluminum, copper, iron, indium, magnesium, manganese, tin, or a combination of two or more of these metals. A preferred alloying metal is copper.

The alloying metal is alloyed with the silicon at a weight percent which promotes separation of nonmetallic contaminants from the alloy. The weight percent of alloying metal employed will depend on the particular alloying metal used and to a lessor extent on the particular nonmetallic contaminants to be separated from the alloy. Generally, a weight percent of alloying metal within a range of about 10 to 90 weight percent of the alloy is considered useful. A lower weight percentage of alloying metal could be used, but may result in reduced separation of nonmetallic contaminants from the alloy. Greater weights of alloying metal can also be used, but to no perceived advantage. Preferred, is where the alloying metal is about 20 to 80 weight percent of the alloy.

The nonmetallic contaminants are separated from the alloy. The nonmetallic contaminants can be separated from the alloy while the alloy is in the molten state or the alloy can be allowed to solidify and the nonmetallic contaminants separated. When the alloy is in the molten state the nonmetallic contaminants can be separated from the alloy by standard methods for separating particulate inclusions from molten metals. The nonmetallic contaminants can be separated from the molten alloy by, for example, filtration, centrifugation, use of a tundish, raking, or skimming.

The method for separating the nonmetallic inclusions from the solidified alloy is not critical to the present invention and can be any method which effects separation of nonmetallic inclusions from the alloy without significant contamination of the recovered nonmetallic inclusions. A flux may be used to facilitate separation of the nonmetallic inclusions from the alloy. The nonmetallic inclusions can be separated from the solidified alloy by, for example, placing the alloy in a liquid media such as water and physically agitating the resultant mixture by, for example, sonification. When separating the nonmetallic inclusions from the solidified alloy by placing in water, it is preferred to add a water soluble flux to the method during the alloying step. The water soluble flux can be, for example, barium chloride or other water soluble materials having low volatility at alloying temperatures. When barium chloride is used as a flux, it is preferred that the barium chloride be at a concentration within a range of about two weight percent to 50 weight percent of the alloy.

The separated nonmetallic contaminants are analyzed for chemical content. The nonmetallic contaminants can be analyzed by standard means for performing physical and elemental analysis of particles. Physical methods include, for example, optical microscopy, SEM, and image analysis. Elemental analyses include, for example, plasma emission, Xray fluorescence, and atomic absorption.

Nonmetallic contaminants recovered and analyzed in the present process are those present in silicon whose separation from the silicon can be promoted by the addition of an alloying metal. The present method is especially useful for analyzing metallurgical grade silicon for oxides and carbides of calcium, aluminum, and silicon.

The present process is useful for analyzing metallurgical grade silicon for nonmetallic contaminants where the metallurgical grade silicon is intended for use in processes, such as, the direct process for the production of organohalosilanes and processes for the production of trichlorosilane.

The following examples are provided to illustrate the present method. These examples are not intended to limit the scope of the present claims.

EXAMPLE 1

Samples of silicon from different lots were evaluated to determine the level of nonmetallic contaminants using copper as an alloying metal to promote separation of nonmetallic contaminants present in the alloy. Barium chloride was used as a water-soluble flux to facilitate separation of the nonmetallic contaminants from the copper-silicon alloy.

Each sample of silicon was tested by forming a mixture comprising 100 g of silicon, 400 g copper, and 20 g $BaCl_2$ in a 250 mL alumina crucible. Silicon sample number 1 was an electronic grade silicon produced by chemical vapor deposition. Silicon samples 2 through 5 were metallurgical grade silicons acquired from commercial silicon producers. The mixture was heated to 1300° C. in an induction furnace under an argon atmosphere. The resulting melt was maintained at 1300° C. for ten minutes, the furnace was turned off, and the melt allowed to solidify forming a copper-silicon alloy ingot containing barium chloride flux. The copper-silicon alloy ingot was transferred to a 400 mL beaker and sufficient water added to completely immerse the ingot. The beaker and contents was placed in an ultrasonic bath for about 30 minutes to dissolve the barium chloride flux and separate insoluble contaminants from the ingot. The insoluble contaminants were recovered by centrifugation and decanting the barium chloride solution. The insoluble contaminants were washed with distilled water, recovered by centrifugation, and air dried in an oven at 110° C. Plasma emission analysis was performed on the insoluble contaminants to determine the aluminum content. Xray diffraction analysis was performed on the insoluble contaminants to determine silicon carbide content. The results are presented in Table 1 as a weight percent (Wt %) of the original silicon sample of 100 g.

In addition, a sample of each of the silicons tested for nonmetallic contaminants was evaluated in a commercial direct process for producing methylchlorosilanes. These results are provided in Table 1 ($Me_2SiCl_2$ Yield (%)) to illustrate the correlation between levels of nonmetallic contaminants in the silicon and performance of the silicon in the direct process. The results for the direct process yield were calculated as: Yield % = $Me_2SiCl_2$ selectivity (Wt %) times the mass fraction of silicon reacted.

TABLE 1

Nonmetallic Contaminants in Silicon and Correlation With Direct Process Performance

| Sample No. | Wt % Al | Wt % SiC | Me$_2$SiCl$_2$ Yield (%) |
|---|---|---|---|
| 1 | 0.001 | na* | na |
| 2 | 0.022 | na | 86.6 |
| 3 | 0.024 | 0.062 | 85.1 |
| 4 | 0.050 | 0.178 | 81.9 |
| 5 | 0.057 | 0.183 | 80.9 | na* = not analyzed

EXAMPLE 2

A sample of metallurgical grade silicon was evaluated to determine the level of nonmetallic contaminants using copper as an alloying metal to promote separation of nonmetallic contaminants present in the alloy. The metallurgical grade silicon tested was from the same lot as silicon number 5 of Example 1. The process was conducted the same as described in Example 1 with the exception that no flux was employed to facilitate separation of the nonmetallic contaminants from the alloy. In this example, to recover the nonmetallic contaminants, the alloy ingot was treated with a dilute aqueous mixture of HF and HNO$_3$. The acid solution was evaporated to dryness to recover solids removed from the ingot. The recovered solids were analyzed by the methods described in Example 1 and the results are given in Table 2.

TABLE 2

Nonmetallic Contaminants in Metallurgical Grade Silicon and Correlation With Direct Process Performance

| Sample No. | Wt % Al | Wt % SiC | Me$_2$SiCl$_2$ Yield (%) |
|---|---|---|---|
| 5 | 0.039 | na | 80.9 |

We claim:

1. A method of analyzing metallurgical grade silicon for nonmetallic contaminants, the method consisting essentially of:
   (A) forming an alloy comprising metallurgical grade silicon and a metal which promotes separation of nonmetallic contaminants present in the alloy,
   (B) separating the nonmetallic contaminants from the alloy, and
   (C) analyzing the separated nonmetallic contaminants for chemical content to determine nonmetallic contaminants present in the metallurgical grade silicon.

2. A method according to claim 1, where the nonmetallic contaminants are separated while the alloy is in a liquid phase.

3. A method according to claim 1, where the nonmetallic contaminants are separated after the alloy is solidified.

4. A method according to claim 3, further comprising the addition of a flux to the alloy while the alloy is molten.

5. A method according to claim 4, where the flux is water soluble.

6. A method according to claim 5, where the flux is barium chloride.

7. A method according to claim 6, where barium chloride is added to the alloy at a concentration within a range of about two weight percent to 50 weight percent of the alloy.

8. A method according to claim 1, where the metal which promotes separation of nonmetallic contaminants present in the alloy is copper.

9. A method according to claim 8, where the alloy is formed at a temperature within a range of about 1300° C. to 1450° C.

10. A method according to claim 1, where the metal which promotes separation of nonmetallic contaminants present in the alloy is selected from a group of metals consisting of aluminum, copper, iron, indium, magnesium, manganese, tin, and a combination of two or more of the metals of the group.

11. A method according to claim 1, where the nonmetallic contaminant is an oxide.

12. A method according to claim 1, where the nonmetallic contaminant is an oxide selected from a group consisting of oxides of aluminum, oxides of calcium, and oxides of silicon.

13. A method according to claim 1, where the nonmetallic contaminant is a carbide.

14. A method according to claim 1, where the nonmetallic contaminant is a carbide selected from a group consisting of carbides of aluminum, carbides of calcium, and carbides of silicon.

15. A method of analyzing metallurgical grade silicon for nonmetallic contaminants, the method consisting essentially of:
   (A) forming at a temperature within a range of about 1300° C. to 1450° C. an alloy comprising metallurgical grade silicon and copper metal at a concentration of copper metal which promote separation of nonmetallic contaminants present in the alloy, where the nonmetallic contaminants are selected from a group consisting of oxides and carbides of calcium, oxides and carbides of aluminum, and oxides and carbides of silicon,
   (B) separating the nonmetallic contaminants from the alloy, and
   (C) analyzing the separated nonmetallic contaminants for chemical content to determine nonmetallic contaminants present in the metallurgical grade silicon.

16. A method of analyzing silicon for nonmetallic contaminants, the method consisting essentially of:
   (A) forming an alloy comprising silicon and a metal which promotes separation of nonmetallic contaminants present in the alloy,
   (B) separating the nonmetallic contaminants from the alloy, and
   (C) analyzing the separated nonmetallic contaminants for chemical content to determine nonmetallic contaminants present in the silicon.

17. A method according to claim 16, where the nonmetallic contaminants are separated after the alloy is solidified.

18. A method according to claim 17, further comprising the addition of a flux to the alloy while the alloy is molten.

19. A method according to claim 18, where the flux is barium chloride.

20. A method according to claim 19, where barium chloride is added to the alloy at a concentration within a range of about two weight percent to 50 weight percent of the alloy.

21. A method according to claim 16, where the metal which promotes separation of nonmetallic contaminants present in the alloy is copper.

22. A method according to claim 21, where the alloy is formed at a temperature within a range of about 1300° C. to 1450° C.

23. A method according to claim 16, where the metal which promotes separation of nonmetallic contaminants present in the alloy is selected from a group of metals consisting of aluminum, copper, iron, indium, magnesium, manganese, tin, and a combination of two or more of the metals of the group.

24. A method according to claim 16, where the nonmetallic contaminant is selected from a group consisting of oxides and carbides of aluminum, oxides and carbides of calcium, and oxides and carbides of silicon.

25. A method of analyzing silicon for nonmetallic contaminants, the consisting essentially of:

(A) forming at a temperature within a range of about 1300° C. to 1450° C. an alloy comprising silicon and copper metal at a concentration of copper metal which promotes separation of nonmetallic contaminants present in the alloy, where the nonmetallic contaminants are selected from a group consisting of oxides and carbides of calciums, oxides and carbides of aluminum, and oxides and carbides of silicon, (B) separating the nonmetallic contaminants from the alloy, and (C) analyzing the separated nonmetallic contaminants for chemical content to determine nonmetallic contaminants present in the silicon.

* * * * *